(12) United States Patent
Sinclair

(10) Patent No.: US 7,077,018 B2
(45) Date of Patent: Jul. 18, 2006

(54) CLEANABLE VOLUME DISPLACEMENT PIPETTER

(75) Inventor: James E. Sinclair, Carlsbad, CA (US)

(73) Assignee: Vertex Pharmaceuticals, Inc., Cambridge, MA (US)

( * ) Notice: Subject to any disclaimer, the term of this patent is extended or adjusted under 35 U.S.C. 154(b) by 56 days.

(21) Appl. No.: 10/833,496

(22) Filed: Apr. 27, 2004

(65) Prior Publication Data

US 2005/0235762 A1    Oct. 27, 2005

(51) Int. Cl.
*B01L 3/02*        (2006.01)
(52) U.S. Cl. .............................. 73/864.13; 73/863.32; 73/864.01; 73/864.11; 73/864.14; 73/864.16; 422/99; 422/100
(58) Field of Classification Search ............. 73/863.31, 73/863.32, 864–864.25; 422/99, 100
See application file for complete search history.

(56) References Cited

U.S. PATENT DOCUMENTS

| 3,290,946 A | * | 12/1966 | Pursell | ..................... 73/864.15 |
| 3,830,108 A | * | 8/1974 | Spong | ..................... 73/864.14 |
| 2001/0004449 A1 | * | 6/2001 | Suzuki et al. | ................ 422/100 |

* cited by examiner

*Primary Examiner*—Hezron Williams
*Assistant Examiner*—David A. Rogers

(57) ABSTRACT

A volume displacement pipette that includes a channel within the piston. The channel allows for cleaning fluids to be continuously run through the pipette tip for cleaning the tip. One end of the channel may be closed during normal operation of the pipette. Multiple pipettes may be combined into an array pipetter.

29 Claims, 4 Drawing Sheets

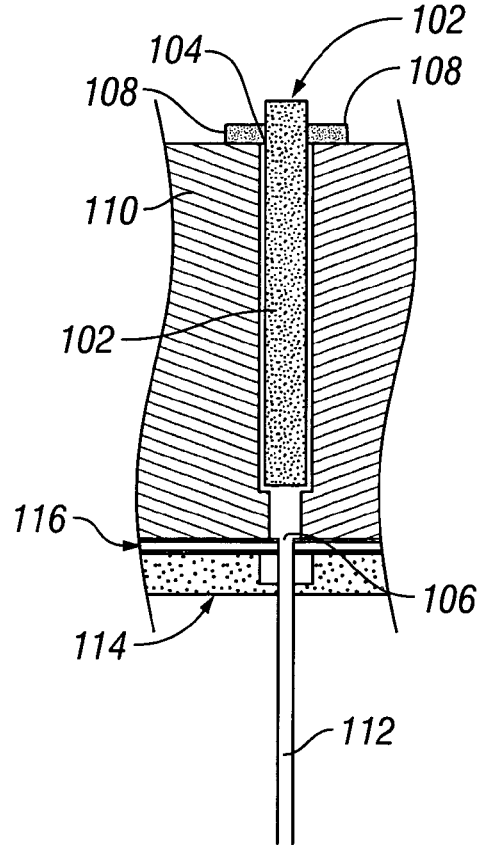
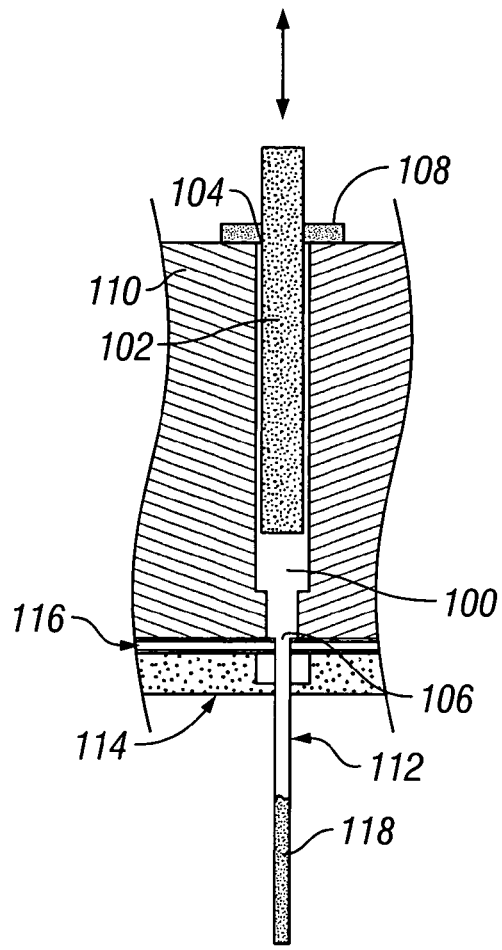
FIG. 1A
*(Prior Art)*
FIG. 1B
*(Prior Art)*

CLEANABLE VOLUME DISPLACEMENT PIPETTER

BACKGROUND OF THE INVENTION

1. Field of the Invention

The present invention relates to the field of scientific instrumentation. More specifically, the present invention relates to pipettes and array pipetters.

2. Description of the Related Art

The widespread adoption by the biotech, pharmaceutical, and life science industry of 96-well plates and its denser 384- and 1536-well descendants has stimulated the concomitant demand for pipetters that can take advantage of these formats. Indeed, there are a variety of fluid-handling devices on the market that are designed to pipette in and out of 96 or 384 wells simultaneously. These array pipetters have 96 or 384 tips arranged in rectangular arrays of 8×12 or 16×24, with 9-mm or 4.5-mm pitch, respectively. There are also devices that only address one column of the plate at a time; this allows for more flexibility at the cost of reduced throughput.

Array pipetters typically are volume displacement devices designed to work in the aspirate-and-dispense mode. Typically a tip, or cannula, is mated to a piston-and-barrel structure with appropriate seals to achieve air-tightness. As the piston moves up, liquid is drawn into the cannula. As the piston moves down, liquid is expelled from the same cannula. This combination of a cannula and piston-barrel is repeated across the array (e.g., 96 or 384 times) to give a pipetting head. For convenience, the cannulae are often assembled into a single tip-carrier to facilitate exchanging one set for another.

This basic design has proved its worth in terms of simplicity, manufacturability, robustness, and versatility. It is adopted by virtually all manufacturers of array pipetters. Yet it suffers from one major defect. Once a reagent has been delivered, the only way to clean out the cannulae is by repeated aspiration and dispensing of a cleaning fluid. Sometimes, sonication is applied to ameliorate the cleaning action. The inside of the cannulae can also be coated with Teflon to reduce adhesion. Despite all these measures, currently available cleaning methods are often not thorough enough and carry-over of reagents becomes a significant problem. When carry-over of reagents must be limited to an absolute minimum, the only existing solution is to replace fixed cannulae with disposable pipette tips. While this is a workable solution, it entails significant cost increases. In addition, throughput is decreased because replacing an entire tip-array is time consuming, especially since it must usually be done manually.

SUMMARY OF THE INVENTION

Disclosed herein is a pipette comprising: a piston barrel coupled to a fluid dispenser/aspirator; a piston disposed within the barrel; and a cleaning channel having a first end in fluid communication with the fluid dispensor/aspirator and a second end in fluid communication with a source of cleaning fluid. In some embodiments a plurality of these pipettes are present in an array pipetter.

Also disclosed herein is a pipette comprising a piston barrel and a piston, wherein the piston comprises a channel extending along its length.

Also disclosed herein is a method of cleaning a pipette that has a barrel and a piston, wherein the method comprises flushing a cleaning fluid through a channel disposed within the piston.

BRIEF DESCRIPTION OF THE DRAWINGS

FIGS. 1A and 1B show a traditional volume displacement pipette.

Figure 2A:
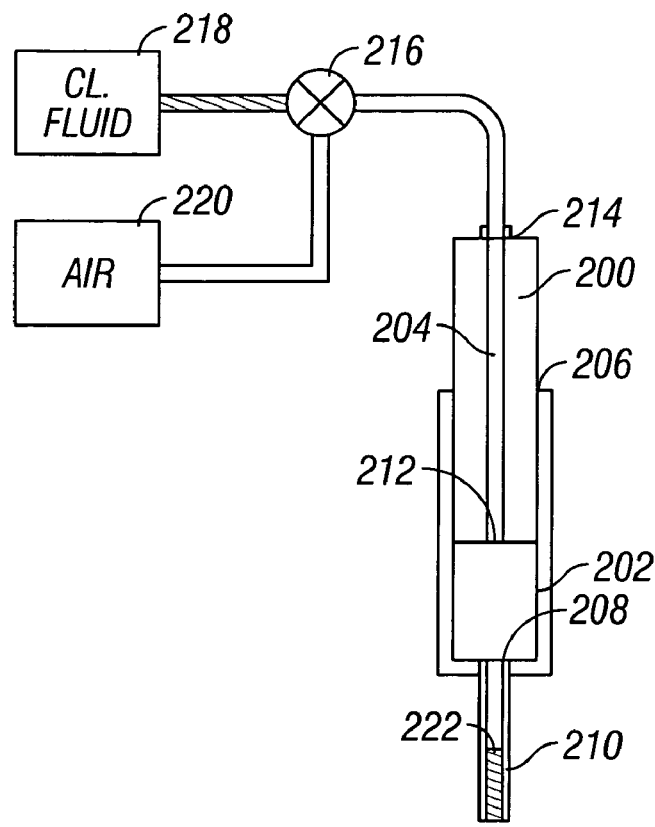
FIGS. 2A and 2B show a volume displacement pipette including a channel allowing for cleaning of the cannula.

A typical pipette design used in array pipetters is depicted in FIGS. 1A and 1B. In this design, a piston barrel 100 is provided. A piston 102 is disposed within the piston barrel 100. The piston barrel 100 typically contains barrel openings 104 and 106 on the ends. The body of the piston 102 extends through opening 104. A seal 108 is provided at opening 104 to ensure that an airtight seal is formed between piston 102, seal 108, and pipette body 110. A cannula 112 is disposed at opening 106 to act as a fluid dispenser/aspirator. Optionally, the cannula 112 may be held in a tip carrier 114. A seal 116 may be used to provide an airtight seal between the seal 116, tip carrier 114, pipette body 110, and cannula 112. In operation, piston 102 can move up, as in FIG. 1B, to draw fluid 118 into cannula 112. Movement of the piston 102 down, as in FIG. 1A, will expel fluid 118 out of cannula 112.

The pipette design depicted in FIGS. 1A and 1B may be used in a single stand alone pipette whose piston 102 is actuated either manually or automatically. Alternatively, a plurality of pipettes such as shown in FIGS. 1A and 1B may be provided to form an array of pipettes. In such a case, a single pipette body 110 may be used with piston barrels 100 formed therein. Furthermore, a single tip carrier 116 may hold all of the cannulae 112. In some embodiments of this array pipetter, each individual piston 102 may be actuated individually. In other embodiments, the pistons 102 are actuated simultaneously. Usually, the pipettes of an array are simultaneously actuated.

As used herein, "array pipetter" refers to any system that comprises more than one pipette assembly. For example, an array pipetter may comprise 96 or 384 pipettes. The multiple pipettes may be arranged in any geometric arrangement.

As discussed above, the design of FIGS. 1A and 1B whether as a single pipette or an array of pipettes, suffers from the drawback that it only allows for cleaning of the cannula 112 by repeated aspiration and dispensing of a cleaning fluid.

In some embodiments, the present invention provides for effective cleaning of pipette cannulae by enabling sustained fluid flow of a cleaning fluid from one end of the cannula and out the other. In some embodiments, this sustained fluid flow is accomplished by providing a channel within the piston of the pipette. The channel allows fluid to flow through the piston and into the cannula. The channel may comprise an opening on the end of the piston near the cannula to enable fluid flow between the cannula and the channel in the piston. An opening on the other side of the piston allows for fluid flow between the channel and a fluid source or sink.

Figure 2B:
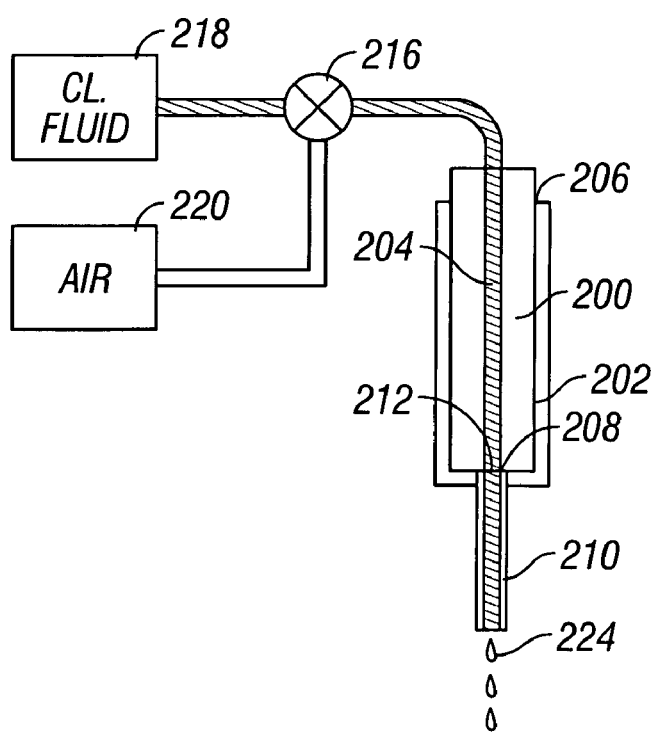

One embodiment of such a pipette is depicted in FIGS. 2A and 2B. The pipette comprises piston 200 disposed within piston barrel 202. A channel 204 runs through piston 200. Piston barrel 202 comprises two openings, 206 and 208. The body of piston 200 extends through opening 206. A cannula 210 is disposed on opening 208. Opening 208 allows for fluid communication between the interior of piston barrel 202 and cannula 210. Channel 204 comprises openings 212 and 214. Opening 212 allows for fluid communication between channel 204 and cannula 210. Opening 214 is connected to valve 216. Valve 216 is connected to a cleaning fluid source 218 and an air source 220. Valve 216 may be positioned to allow fluid communication between cleaning fluid source 218 and channel 204 or to allow fluid communication between air source 220 and channel 204. Alternatively, valve 216 may be closed such that neither cleaning fluid 218 nor air source 220 is in fluid communication with channel 204.

For normal pipette operation, depicted in FIG. 2A, valve 216 is advantageously closed. The seal formed by closed valve 216 allows reagent fluid 222 to be drawn into cannula 210 when piston 200 is raised. Similarly, when piston 200 is lowered, reagent fluid 222 will be expelled from cannula 210 as long as valve 216 is closed.

For cleaning operation, depicted in FIG. 2B, valve 216 may be opened to cleaning fluid source 218 allowing cleaning fluid 224 to flow through channel 204 into and out of cannula 210 in order to clean the cannula 210. After sufficient cleaning, valve 216 may be opened to air source 220 to allow any cleaning fluid 224 remaining in cannula 210 to be dried. Alternatively, air source 220 may be used without prior use of cleaning fluid 224 to dry reagent fluid 222 in cannula 210. It is advantageous that piston 200 be driven all the way down during cleaning as in FIG. 2B to prevent cleaning fluid from contaminating the sides of piston barrel 202.

Figure 3A:
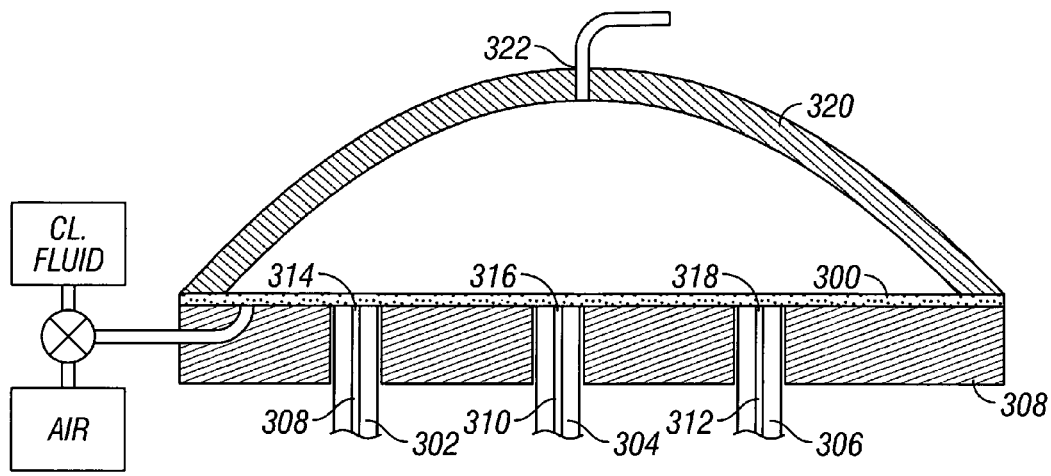
FIGS. 3A and 3B show a portion of an array pipetter that includes cleaning channels and a flexible membrane.
Figure 3B:
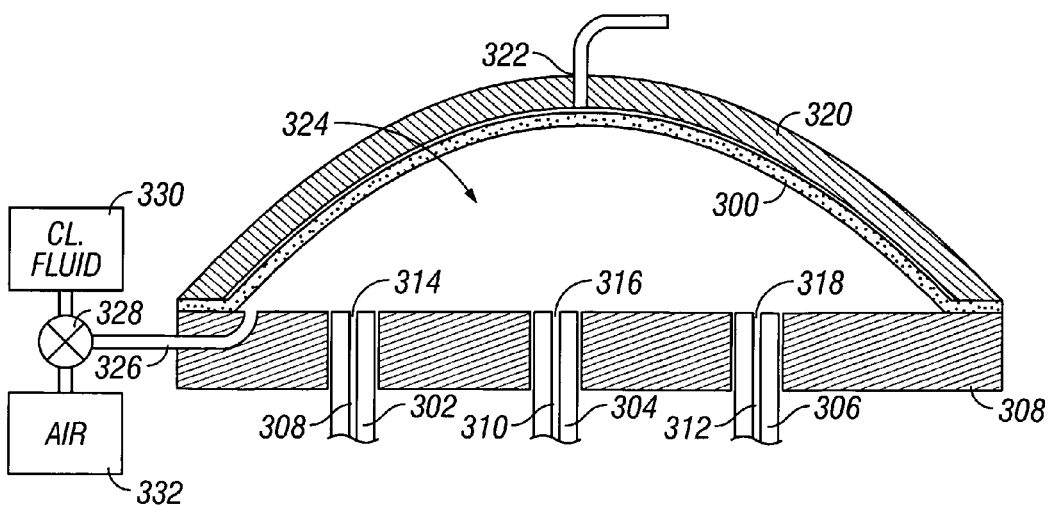

In some embodiments, the general pipette design described above may be repeated to form an array pipetter. In some embodiments, valves such as depicted in FIGS. 2A and 2B may be used for each pipette within the array pipetter. In other embodiments, a single valve may operate to open and close all piston channels. Such a design is depicted in FIGS. 3A and 3B. In this design, a control mechanism to open and close the piston channels is provided by a flexible membrane 300. The top portions of a plurality of pistons 302, 304, and 306 are secured within holes in a piston end plate 308. The lower part of the pistons 302, 304, and 306 extend into piston barrels (not shown). Piston channels 308, 310, and 312 run through pistons 302, 304, and 306 respectively. The piston channels 308, 310, and 312 have top openings 314, 316, and 318. The ends of a curved top plate 320 secures the top plate 320 to the ends of membrane 300 and the piston end plate 308. While a curved top plate is advantageous in order to minimize trapped air bubbles, top plate 320 may have any shape. A seal is formed between top plate 320 and membrane 300 and between piston end plate 308 and membrane 300. A pressure-based control inlet 322 is provided through top plate 320.

The flexible membrane 300 operates to close channels 308, 310, and 312 when pressure is applied through pressure control inlet 322, as depicted in FIG. 3A. Pressure may be applied by directing pressurized air through pressure control inlet 322. When this occurs, membrane 300 is pressed against channel openings 314, 316, and 318, forming a seal over the openings 314, 316 and 318. The array pipetter may then be used for normal pipette operation.

Flexible membrane 300 may be opened by applying a vacuum to pressure control inlet 322, as depicted in FIG. 3B. The vacuum causes flexible membrane 300 to be pulled up against top plate 320, thus breaking the seal between the membrane 300 and the channel openings 314, 316, and 318. This operation also defines a cavity 324 that is in fluid communication with piston channels 308, 310, and 312. An inlet 326 that extends through piston end plate 308 is also in fluid communication with cavity 324. The inlet 326 may be connected to a valve 328 that operates to close inlet 326 or open it to cleaning fluid source 330 or air source 332. For cleaning operation, cleaning fluid can flow from cleaning fluid source 330 through inlet 326 to flood cavity 324 and flow through pipette channels 308, 310, and 312, thus forcing cleaning fluid through the pipette cannulae (not shown). Similarly, air can flow from air source 332 through inlet 326, into cavity 324, and through channels 308, 310, and 312 to dry the cannulae (not shown). It will be appreciated that the design of FIGS. 3A and 3B allows for a single fluid inlet for all pipettes within the array pipetter.

Figure 4C:
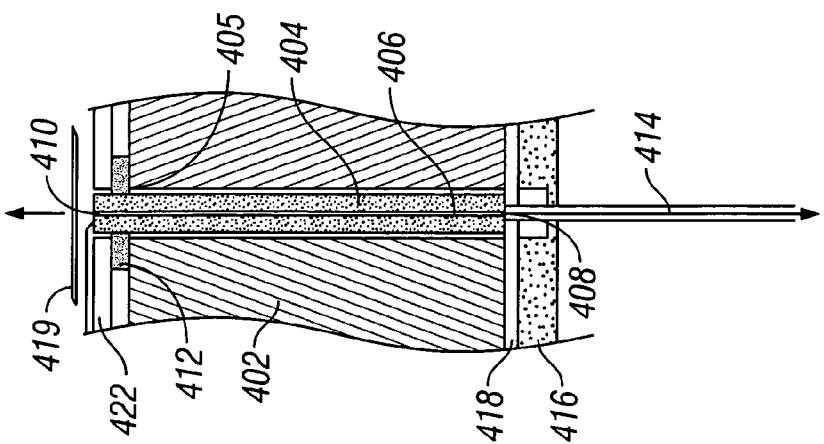
FIGS. 4A through 4C show the operation of an array pipetter with cleaning channels and a flexible membrane.
Figure 4B:
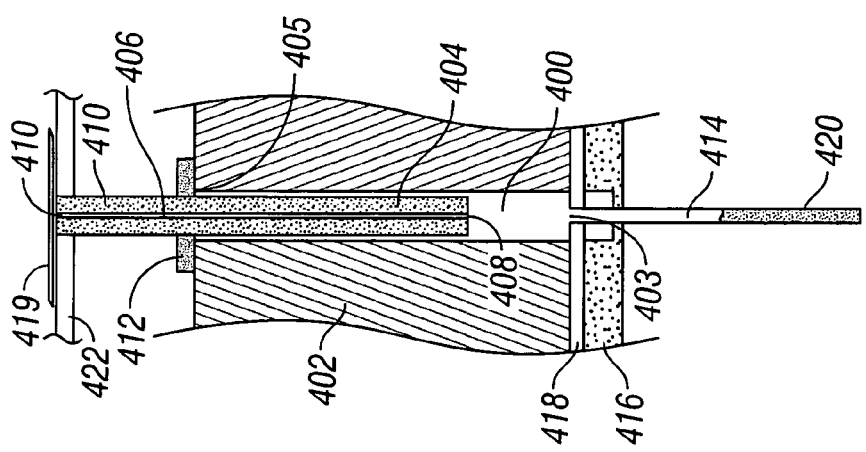
Figure 4A:
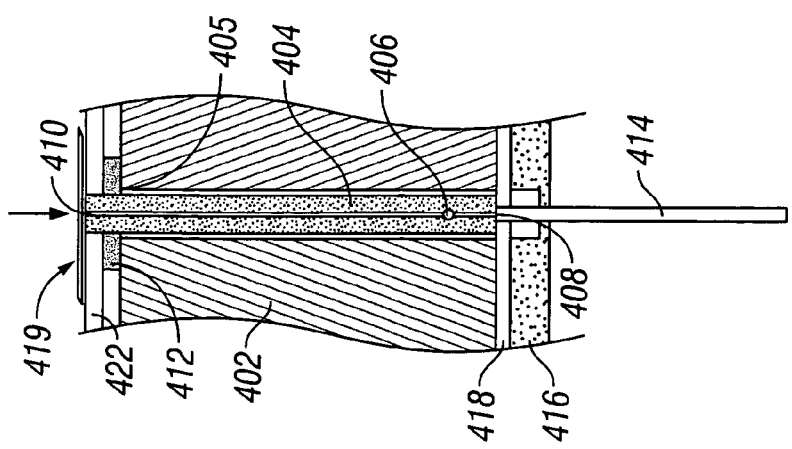

A single pipette within an array pipetter according to FIGS. 3A and 3B is depicted in FIG. 4. A piston barrel 400 is formed within pipette body 402. The pipette cavity 400 has openings 403 and 405. A piston 404 is disposed within the pipette cavity 400 and extends through opening 405. A channel 406 runs through piston 404. An opening 408 in channel 406 is provided on the end of piston 404 that is within piston barrel 400. A second opening 410 in channel 406 is provided on the opposite end of piston 404. As in the design of FIG. 1, a seal 412 is provided to maintain an airtight seal between piston 404, pipette body 402, and seal 412. A cannula 414 is disposed over opening 403 to act as a fluid dispenser/aspirator. A tip carrier 416 may hold the cannula 414. A seal 418 may be provided to form an airtight seal between seal 418, tip carrier 416, cannula 414, and pipette body 402.

The array pipetter in FIG. 4 comprises the flexible membrane 419 and pipette end plate 422 that is depicted in more detail in FIGS. 3A and 3B. As described above, when pressure is exerted against membrane 419, as depicted in positions A and B in FIG. 4, a seal is formed between membrane 419 and piston 404. When pressure is reduced on membrane 419, such as by using a vacuum as depicted in position C in FIG. 4, the seal is broken allowing fluid communication between channel 406 and the space above channel opening 410. The pressure on membrane 419 may be controlled by any suitable means. Some means include controlling the air pressure above membrane 419 as depicted in FIGS. 3A and 3B or providing a mechanism for applying mechanical pressure to membrane 419.

When the pipette of FIG. 4 is to be used for normal pipette fluid withdrawing and dispensing, membrane 418 advantageously forms a seal over piston channel opening 410. Thus, as depicted in position B of FIG. 4, the piston 404 can be moved up to draw fluid 420 into cannula 414. Similarly, when membrane 419 forms a seal, the piston can be moved down, as in position A of FIG. 4 to expel fluid from cannula 414. Because piston end plate 422 is fixed to piston 404, piston end plate 422, membrane 419, and the rest of the assembly as described in FIGS. 3A and 3B moves with the piston 404.

When the cannula 414 is to be cleaned, the seal formed by membrane 418 is broken by reducing pressure on membrane 418 as described above. Cleaning fluid can then be forced through channel 406 and cannula 414. It is preferable during cleaning to drive piston 406 all the way down, as in position C in FIG. 4, such that there is no empty space within piston barrel 400. Such a position inhibits cleaning fluid from contacting and contaminating the sides of piston barrel 400. It will be recognized that in general, cleaning fluid may either flow from opening 410 through the cannula 414 or from cannula 414 to opening 410. When used as depicted in FIGS. 3A and 3B, cleaning fluid flows from opening 410 through cannula 414.

As depicted in FIGS. 3A and 3B, the array pipetter may have a single fluid inlet to supply cleaning fluid to all channels 406. The flow rate in channels 406 having the same diameter has been found to vary by less than two times regardless of the location of the single fluid inlet. In some embodiments, the resistance to flow in the channels 406 may be varied between the channels 406 such that the flow rate through the channels 406 is substantially uniform. Methods of varying fluid resistance include varying the diameter of the channels 406 or varying the diameter of channel openings 410 or 408.

In an alternative embodiment, the pipette array may be constructed such that pressure may be applied to membrane 410 individually over each channel opening 410 to provide individual control to piston channels 406. In some alternative embodiments, each individual piston 404 may be actuated individually.

Cleaning substances for use herein include any of those known in the art and may be varied depending on the substance to be cleaned from the cannulae. Typical cleaning substances include water, detergent, acid, acetone, or other organic solvents. Multiple cleaning substances may be used in series to achieve the desire level of decontamination. Furthermore, a gas may be used to dry the cannulae, either as the sole means of cleaning or after applying a liquid cleaning substance. Typical gases that may be used include air, nitrogen, or argon.

It will be recognized to those of skill in the art that the cleaning channel described herein may be used for purposes other than cleaning fluids. For example, reagents may be dispensed through the channels. The pipette may be connected to multiple supplies of reagents with appropriate switching valves for selecting the appropriate reagent source.

It will be further recognized to those of skill in the art that geometries other than that depicted in FIGS. 2–4 may be used. For example, the pistons and piston barrels may have shapes other than cylindrical. Similarly, the piston channels need not be cylindrical. In some embodiments, the channel could be a groove in the side of the piston or could be drilled through the pipette body. In addition, the piston channel openings may be located in positions other than on the ends of the pistons. For example, the openings may be located on the side of the pistons. While the flexible membrane described herein is advantageous, any suitable valve means may be used for closing piston channel opening.

What is claimed is:

1. A pipette comprising:
   a piston barrel coupled to a fluid dispenser/aspirator;
   a piston disposed within said barrel and configured to dispense and aspirate fluid with said fluid dispenser/aspirator via motion within said barrel; and
   a cleaning channel formed in or through said piston having a first end in fluid communication with said fluid dispensor/aspirator and a second end in fluid communication with a source of cleaning fluid.

2. The pipette of claim 1 wherein said cleaning fluid operates to clean said fluid dispenser/aspirator.

3. The pipette of claim 1 wherein said cleaning fluid operates to dry said fluid dispenser/aspirator.

4. The pipette of claim 1 wherein said piston barrel and said piston are cylindrical in shape.

5. The pipette of claim 1 wherein said cleaning channel is cylindrical in shape.

6. The pipette of claim 1 further comprising a valve configured to open and close said cleaning channel to said source of cleaning fluid, wherein when said valve is open, cleaning fluid flows from said source of cleaning fluid to said fluid dispenser/aspirator through said cleaning channel.

7. The pipette of claim 6 wherein said cleaning channel runs through said piston.

8. The pipette of claim 6 wherein when cleaning fluid flows from said source of cleaning fluid to said fluid dispenser/aspirator, said piston is positioned to fill said piston barrel such that cleaning fluid does not contact the surfaces of said piston barrel.

9. A pipette comprising:
   a piston barrel coupled to a fluid dispenser/aspirator;
   a piston disposed within said barrel and configured to dispense and aspirate fluid with said fluid dispenser/aspirator via motion within said barrel;
   a cleaning channel formed through said piston having a first end in fluid communication with said fluid dispensor/aspirator and a second end in fluid communication with a source of cleaning fluid;
   a valve configured to open and close said cleaning channel to said source of cleaning fluid, wherein when said valve is open, cleaning fluid flows from said source of cleaning fluid to said fluid dispenser/aspirator through said cleaning channel and wherein said cleaning channel runs through said piston; and
   a flexible membrane disposed adjacent to said second end.

10. The pipette of claim 9 wherein said valve is closed by increasing pressure on said flexible membrane.

11. The pipette of claim 9 wherein said valve is opened by reducing pressure on said flexible membrane.

12. An array pipetter comprising a plurality of pipettes at least one of said plurality of pipettes comprising:
    a piston barrel coupled to a fluid dispenser/aspirator;
    a piston disposed within said barrel and configured to dispense and aspirate fluid with said fluid dispenser/aspirator via motion within said barrel; and
    a cleaning channel having a first end in fluid communication with said fluid dispensor/aspirator and a second end in fluid communication with a source of cleaning fluid.

13. The array pipetter of claim 12 wherein said cleaning channel runs through said piston.

14. The array pipetter of claim 12 wherein said plurality of pipettes are arranged in an 8 by 12 array.

15. The array pipetter of claim 12 wherein said plurality of pipettes are arranged in an 16 by 24 array.

16. An array pipetter comprising a plurality of pipettes, wherein at least one pipette comprises:
    a piston barrel coupled to a fluid dispenser/aspirator;
    a piston disposed within said barrel;
    a cleaning channel formed in or through said piston having a first end in fluid communication with said fluid dispensor/aspirator and a second end in fluid communication with a source of cleaning fluid; and
    a flexible membrane disposed adjacent to all of said second ends.

17. The array pipetter of claim 16 wherein pressure is applied to said opposite side of said flexible membrane to create a seal over all of said second ends.

18. The array pipetter of claim 16 wherein pressure is applied to said opposite side of said flexible membrane to create a seal over less than all of said second ends.

19. The array pipetter of claim 16 wherein pressure is reduced on said opposite side of said flexible membrane to prevent a seal from forming over less than all of said second ends.

20. The array pipetter of claim 16 wherein pressure is reduced on said opposite side of said flexible membrane to prevent a seal from forming over all of said second ends.

21. The array pipetter of claim 20 wherein said cleaning channels are in fluid communication with each other.

22. The array pipetter of claim 21 wherein cleaning fluid flows from said source of cleaning fluid to all of said fluid dispenser/aspirators through said cleaning channels.

23. The array pipetter of claim 22 wherein flow resistance through said cleaning channels varies such that flow rate through each of said cleaning channels is substantially the same.

24. The array pipetter of claim 23 wherein flow resistance is varied by varying the diameter of each of said cleaning channels relative to each other.

25. A method of processing liquid samples comprising:
aspirating and dispensing a first liquid with a pipette tip by moving a piston within a barrel so as to pull said first liquid into said pipette tip and push said first liquid out from said pipette tip;
opening a channel in or through said piston;
cleaning said pipette tip by routing cleaning fluid through said channel and out said pipette tip;
closing said channel; and
aspirating and dispensing a second liquid with a pipette tip by moving a piston within a barrel so as to pull said second liquid into said pipette tip and push said second liquid out from said pipette tip.

26. The method of claim 25, wherein said cleaning fluid is a liquid.

27. The method of claim 25, wherein said cleaning fluid is a gas.

28. The method of claim 25, wherein said second liquid has a different composition than said first liquid.

29. The method of claim 25, wherein opening said channel comprises moving a flexible membrane away from an end of said piston.

\* \* \* \* \*

UNITED STATES PATENT AND TRADEMARK OFFICE
CERTIFICATE OF CORRECTION

| | | |
|---|---|---|
| PATENT NO. | : 7,077,018 B2 | Page 1 of 1 |
| APPLICATION NO. | : 10/833496 | |
| DATED | : July 18, 2006 | |
| INVENTOR(S) | : James E. Sinclair | |

It is certified that error appears in the above-identified patent and that said Letters Patent is hereby corrected as shown below:

Column 2, Line 16, Before "A typical pipette" insert -- Detailed Description of the Preferred Embodiment --

Column 6, Line 34, In Claim 12, delete "pipettes" and insert -- pipettes, --, therefor.

Signed and Sealed this

Tenth Day of April, 2007

JON W. DUDAS
*Director of the United States Patent and Trademark Office*